United States Patent
Whiting et al.

(10) Patent No.: US 8,277,781 B2
(45) Date of Patent: Oct. 2, 2012

(54) DEVICE FOR INTRANASAL ADMINISTRATION

(75) Inventors: Roger Whiting, Los Altos, CA (US); Ramachandran Thirucote, Atherton, CA (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 568 days.

(21) Appl. No.: 12/404,250

(22) Filed: Mar. 13, 2009

(65) Prior Publication Data

US 2010/0233099 A1  Sep. 16, 2010

(51) Int. Cl.
*A61K 9/00* (2006.01)
*A61M 11/00* (2006.01)

(52) U.S. Cl. .............. 424/45; 128/200.14; 128/203.22

(58) Field of Classification Search .............. 424/45; 128/200.14, 203.22
See application file for complete search history.

(56) References Cited

U.S. PATENT DOCUMENTS

| | | | |
|---|---|---|---|
| 4,089,969 A | 5/1978 | Muchowski et al. | |
| 4,150,744 A | 4/1979 | Fennimore | |
| 4,778,810 A | 10/1988 | Wenig et al. | |
| 4,885,287 A | 12/1989 | Hussain et al. | |
| 4,943,587 A | 7/1990 | Cetenko et al. | |
| 4,994,439 A | 2/1991 | Longenecker et al. | |
| 5,143,731 A | 9/1992 | Viegas et al. | |
| 6,090,368 A | 7/2000 | Zia et al. | |
| 6,333,044 B1 | 12/2001 | Santus et al. | |
| 6,390,291 B1 | 5/2002 | Garrill et al. | |
| 2002/0061281 A1 | 5/2002 | Osbakken et al. | |
| 2003/0022894 A1 | 1/2003 | Serno et al. | |
| 2005/0034723 A1 | 2/2005 | Bennett et al. | |
| 2008/0220107 A1 | 9/2008 | Akerman | |
| 2009/0011051 A1* | 1/2009 | Roth et al. | 424/699 |
| 2009/0042968 A1 | 2/2009 | Whiting et al. | |

FOREIGN PATENT DOCUMENTS

| | | |
|---|---|---|
| EP | 0 272 097 | 12/1987 |
| EP | 0 242 643 | 3/1992 |
| EP | 0524587 A1 | 1/1993 |
| GB | 2 315 673 | 2/1998 |

OTHER PUBLICATIONS

U.S. Appl. No. 12/722,137, filed Mar. 11, 2010, Whiting et al.
U.S. Appl. No. 12/483,586, filed Jun. 12, 2009, Whiting et al.
Buckley, M., et al., "Ketorolac, A review of its pharmacodynamic and pharmacokinetic properties, and therapeutic potential", *Drugs* 39(1):86-109, 1990.
Reuben, S., et al., "An evaluation of the analgesic efficacy of intravenous regional anesthesia with lidocaine and Ketorolac using a forearm versus upper arm tourniquet", *Anesth. Analg.* 95:457-60, 2002.
Santus, G., "Nasal Formulations of Ketorolac Tromethamine: Technological Evaluation—Bioavailability and Tolerability in Rabbits", *IL Farmaco*, 48(12):1709-1723, 1993.
Chien, Y. et al., "Historic Development of Transnasal Systemic Medications," *Transnasal Systemic Medications*, (2 pgs.) Amsterdam, 1985.
Mroszczak, E. et al., "Ketorolac Tromethamne Absorption, Distribution, Metabolism, Excretion, and Pharmacokinetics in Animals and Humans", *Drug Metab. Dispos.* 15(5) 618-626, 1987.
Ceschel, G. et al., "Nasal Delivery System", *Speciale Farmaceutica*, 488-493, 1993.
Quadir, M. et al., "Development and Evaluation of Nasal Formulations of Ketorolac," *Drug Delivery*, 7:223-229, 2000.

* cited by examiner

*Primary Examiner* — Mina Haghighatian
(74) *Attorney, Agent, or Firm* — Foley & Lardner LLP

(57) ABSTRACT

Disclosed herein are devices and processes for preparing a vial for an intranasal administration of a medicament where the vial comprises reduced oxygen content.

6 Claims, 6 Drawing Sheets

DEVICE FOR INTRANASAL ADMINISTRATION

FIELD OF THE INVENTION

Disclosed herein are vials and methods for preserving a ketorolac composition where each vial comprises a head space with reduced oxygen content.

BACKGROUND

Ketorolac has been known for several years (U.S. Pat. No. 4,089,969) and is used in human therapy as an analgesic and an anti-inflammatory as the tromethamine salt. U.S. Pat. No. 4,089,969 is incorporated herein by reference in its entirety.

Ample literature is available on ketorolac (for instance, "Ketorolac—A review of its pharmacodynamic and pharmacokinetic properties and its therapeutic potential", Drugs 39(1): 86-109, 1990). It is described as a drug with considerably higher analgesic activity than many other non-steroidal anti-inflammatory drugs. Most significantly, it has analgesic activity comparable to that of the opiates, such as morphine, without the well-known side effects of the latter.

It is known that ketorolac can be formulated as a nasally administrable composition. See U.S. Pat. No. 6,333,044 to Recordati, and U.S. Patent Application Publication No. 2009/0042968, which are incorporated herein by reference in their entirety.

Administering ketorolac tromethamine nasally has certain advantages over administering the compound by injection or orally. These are discussed in prior art references U.S. Pat. No. 6,333,044 and U.S. Patent Publication 2009/0042968. The latter reference teaches that ketorolac tromethamine is successfully combined with a local anesthetic, e.g. lidocaine hydrochloride, to reduce the stinging effect that some patients experience with the nasal administration of ketorolac tromethamine alone.

SUMMARY OF THE INVENTION

In one aspect, this invention provides a vial capped with a spray system, the vial comprising: a solution, a dip tube attached to the spray system and dipping into the solution, and a head space above the solution, wherein the head space comprises no more than about 10% v/v oxygen.

In another aspect, this invention provides a nasal spray device, comprising: a vial and a nasal spray system capped to the vial wherein the vial comprises a solution, a dip tube attached to the nasal spray system and dipping into the solution, and a head space above the solution, wherein the head space comprises no more than about 10% volume to volume (v/v) oxygen.

In still another aspect, this invention provides a high recovery vial capped with a spray system, comprising a concave or V shaped inner bottom. In some embodiments, the high recovery vial further comprises a head space above the solution, wherein the head space comprises equal to or less than about 10% v/v oxygen.

These and the other embodiments are further described in the text that follows.

BRIEF DESCRIPTION OF THE DRAWINGS

This invention will be further described with reference being made to the accompanying drawings.

DETAILED DESCRIPTION OF THE INVENTION

Figure 1:
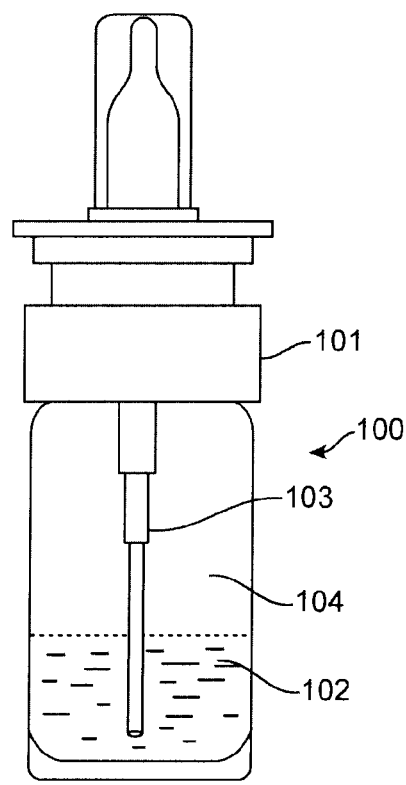
FIG. 1 illustrates an example of a vial, preferably with a head space comprising equal to or less than about 10% v/v oxygen.

Before the various aspects of this invention are described, it is to be understood that the invention is not limited to the particular methodologies, protocols, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

In accordance with the present invention and as used herein, the following terms are defined with the following meanings, unless explicitly stated otherwise.

The term "about" when used before a numerical designation, e.g., pH, temperature, amount, concentration, and molecular weight, including range, indicates approximations which may vary by (+) or (−) 5%, 1% or 0.1%.

As used in the specification and claims, the singular form "a", "an" and "the" include plural references unless the context clearly dictates otherwise. For example, the term "a pharmaceutically acceptable salt" includes a plurality of pharmaceutically acceptable salts, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace amount of elements of other ingredients and substantial method steps. Embodiments defined by each of these transition terms are within the scope of this invention.

"Ketorolac" refers to the chemical compound of 5-benzoyl-2,3-dihydro-1H-pyrrolizine-1-carboxylic acid which has the following Formula (I):

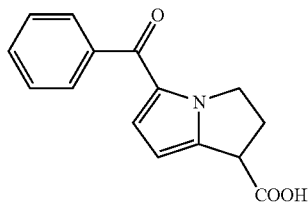

(I)

or a pharmaceutically acceptable salt thereof.

For purposes of this application, the name ketorolac encompasses individually or collectively the racemic mixture, a scalemic (or enantiomerically enriched) mixture, or optically active compound as well as tautomers thereof, and includes the pharmaceutically acceptable salts of ketorolac, particularly the tromethamine salt. As used herein, a racemic mixture of ketorolac is a mixture having equal amounts of the two enantiomers of Formula (I). A scalemic or enantiomerically enriched mixture of ketorolac is a mixture where the amount of one of the enantiomers of Formula (I) is larger than the other enantiomer. An optically active compound may include enantiomerically enriched or enantiomerically pure compound. Enantiomerically pure compound refers to ketorolac having more than 99%, e.g. 99.5%, or 99.9% of one of the enantiomers relative to the total amount of ketorolac.

"Lidocaine" refers to the chemical compound of 2-(diethylamino)-N-(2,6-dimethylphenyl)acetamide, which has the Formula (II):

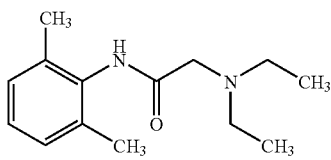

(II)

or a pharmaceutically acceptable salt thereof.

Many pharmaceutically acceptable salts of lidocaine are known. Non-limiting examples of such salts are lidocaine hydrochloride and lidocaine methanesulphonate. As used herein, the term "lidocaine" refers to the compound or any of its pharmaceutically acceptable salts, unless otherwise indicated.

The term "subject," "individual" or "patient" is used interchangeably herein, and refers to a human.

The term "pharmaceutically acceptable salt" refers to pharmaceutically acceptable salts derived from a variety of organic and inorganic counter ions well known in the art and include, by way of example only, sodium, potassium, calcium, magnesium, ammonium, tromethamine and tetraalkylammonium, and when the molecule contains a basic functionality, salts of organic or inorganic acids, such as hydrochloride, hydrobromide, tartrate, mesylate (methanesulfonate), acetate, maleate, and oxalate. Suitable salts include those described in P. Heinrich Stahl, Camille G. Wermuth (Eds.), Handbook of Pharmaceutical Salts Properties, Selection, and Use; 2002.

Device

One aspect of this invention is a device, such as a vial, comprising a volume of about 10 mL or less associated with a spray system for delivering a medicament to a subject from a solution containing the medicament. Such a vial will generally be capped with the spray system and will have a headspace between the surface of the solution and the cap. We have found that the content of the gas occupying the headspace above the solution where the medicament is ketorolac need to be kept below 10% v/v oxygen to ensure the long term stability of the ketorolac solution without the need of refrigeration.

Our ambient atmosphere (air) contains about 20% v/v oxygen, 78% nitrogen, 1% argon, and a number of other components. It has been found that high oxygen content can degrade certain medicament solutions (e.g. ketorolac tromethamine) in the vial thereby reducing the shelf life of the medicament. Under such circumstances, the solution-containing vial is often kept refrigerated to maintain stability of the solution over the desired shelf life of the product. The need for refrigeration can increase the cost of handling and storing of the product.

We have found that ketorolac can produce several degradation products, such as the 1-keto analog having Formula (III) and the chemical name of 5-benzoyl-2,3-dihydro-1H-pyrrolizin-1-one (or 5-benzoyl-1-keto-2,3-dihydro 1H-pyrrolizine, in racemic or optically active form), in solution.

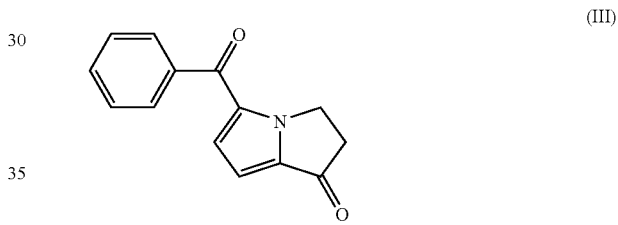

(III)

The 1-keto analog forms when ketorolac is oxidized by too much oxygen in the headspace of the device. We have found that the formation of the 1-keto analog is especially problematic for the intranasal compositions with a high concentration of ketorolac. Prior to the discovery of intranasally administered ketorolac, it has been available for parenteral administration at a much lower concentration in the order of about 3% or 1.5% or less. A lower concentration is used because a larger volume can be administered over time. At this lower concentration, the amount of 1-keto analog formed is within an acceptable level. However, due to the limited volume that can be administered intranasally, a much higher concentration of ketorolac is required, which we found can result in a concentration of the 1-keto analog that can be outside the acceptable level, which may cause safety concerns. It has been discovered that by ensuring that there is less than 10% v/v oxygen in the head space of the vial containing a highly concentrated ketorolac tromethamine solution, the shelf life of the final product is extended without the need for refrigeration. The unique product of this invention may be obtained by a manual process, as discussed hereinafter, or by a unique oxygen reduction device provided herein that reduces the level of oxygen content in the vial containing the intranasal formulation thereby reducing the level of the ketorolac degradative products and resulting in a device providing a level of stability that allows the formulation to be stored at room temperatures for two years or more.

The ketorolac solution for intranasal administration is contained and stored in a container, referred to herein as a vial.

Owing to a limited volume of the solution in the vial, there is often head space left in the vial. Typically, this head space is filled with air having about 20% v/v oxygen. In many cases, it is not practical to reduce the head space volume to an extent that the amount of air is not a substantial issue to the stability of the medicament inside the vial. In most cases, the head space increases as the medicament is expelled from the vial. For example, in the case of a vial containing an intranasal composition, the head space volume is typically determined by the following factors:

(1) The size of the vial: Due to the presence of the spray system on the vial in order to deliver the composition by intranasal spray, the minimum size of the vial needs to be able to balance the weight of the spray system in order to stabilize the vial when the vial is stored. If the vial is too small, the vial will tend to tip over and fall due to the weight of the spray system. Preferably the minimum volume of the vial is about 3.5 mL. Preferably, the maximum volume of the vial is about 10 mL, more preferably 5 mL.

(2) The volume of the composition inside: In a preferred embodiment, the amount of drug solution that may be contained in a single vial is about 0.4-4 mL; more preferably about 0.6-3 mL; and even more preferably about 0.8-2 mL. In one embodiment the volume is about 1 mL and up to about 1.8 mL. In another embodiment the volume is not less than about 1.6 mL and up to about 1.8 mL.

Accordingly, the minimum head space is dictated by the size of the vial and the volume of the solution contained therein and generally about 1 mL, 3 mL, 4 mL or larger, which, if filled with air will contain an oxygen amount that may cause significant degradation of the drug contained in the vial. Generally, the headspace is no more than 80% of the total volume of the vial.

Thus it can be seen that the invention, based on this line of discoveries and observations of the inventor, comprises several aspects. One aspect is a product for nasal administration of a solution of ketorolac, and optionally lidocaine, which is contained in a vial fitted with an atomizer and having a headspace that contains less than 10% v/v oxygen. Another aspect of this invention is a method of administering ketorolac, alone or in combination with lidocaine, by nasal administration using the product. Another aspect of the invention is a method of making the product of the invention by placing a solution of ketorolac, and optionally lidocaine, into a vial containing a suitable amount of the solution for nasal administration, ensuring that the headspace of the vial has less than 10% v/v of oxygen, and capping the vial. Still another aspect of the invention is a system for treating pain or inflammation in a human that comprises the product in combination with labeling instructions for such use. Other aspects of the invention will apparent to one of ordinary skill in the art upon reading this application in its entirety.

Accordingly, in one aspect, there is provided a vial capped with a spray system, the vial comprising: a solution, a dip tube attached to the spray system and dipping into the solution, and a head space above the solution, wherein the head space comprises equal to or less than about 10% v/v oxygen.

An example of the vial capped with a spray system, is illustrated in FIG. 1. The vial 100 in FIG. 1 is shown for illustration purposes only and it is to be understood that any variation in the size, shape, or design of the vial is well within the scope of the present invention. The vial 100 may be made of glass, polymer, or any other suitable material known in the art. The vial 100 comprises a cap 101 which is a spray system. In some embodiments, the spray system is a nasal spray system. In some embodiments, the nasal spray system is a metered nasal spray system.

The vial 100 comprises a solution 102 in the vial. In some embodiments, the solution 102 is a medicament. In some embodiments, the medicament comprises a ketorolac solution as described in one or more of U.S. Pat. No. 6,333,044, U.S. Patent Application Publication No. 2009/0042968, U.S. Provisional Application No. 61/061,522, filed on Jun. 13, 2008, titled, "Unit Dose Formulations of Ketorolac and Lidocaine Combination for Intranasal Administration," and U.S. Provisional Application No. 61/160,254, filed Mar. 13, 2009 on even date herewith and entitled, "Unit Dose Formulations of Ketorolac for Intranasal Administration," all of which are incorporated herein by reference in their entirety. In some embodiments, the vial contains multiple unit doses of the ketorolac solution. In some embodiments, the vial contains up to 8 unit doses of the ketorolac solution.

The vial 100 comprises a dip tube 103 in the vial that is attached to the spray system at one end and is dipping in the solution at the other end. The vial 100 also comprises a head space 104 in the vial where the head space comprises an inert gas with no more than about 10% v/v oxygen. In some embodiments, the head space comprises an inert gas with no more than about 8% v/v oxygen; or more preferably no more than about 5% v/v oxygen. In some embodiments, the head space comprises an inert gas having between about 5% to about 10% v/v oxygen; or between about 3% to about 8% v/v oxygen; or between about 2% to about 5% v/v oxygen.

Keeping the percentage of oxygen the head space to 10% or less keeps the solution stable for about two years. It is to be understood that "stable" describes a state that the solution remains substantially unchanged in the percentage of active ingredient in solution so that it is suitable for its intended use during the relevant period of time. For example, if the solution is a medicament, the solution is in a stable state if it meets the standard for being used as a medicament as requested by a New Drug Application applicant and required by the relevant regulatory agency, such as the United States Food and Drug Administration. Thus, a stable solution may comprise certain minor degree of degradation, so long as the degree of degradation is not significant enough to make it unusable for its intended use, e.g., fall below the standard for use as a medicament. In some embodiments, the solution in the vial can be stored in the vial for about two years at room temperature. In some embodiments, no more than about 10% v/v oxygen in the head space increases the shelf life of the solution as compared to the vial containing an ambient atmosphere. Where the vial contains highly concentrated ketorolac solution, e.g., 12-38% or 15-35% w/v, storing the ketorolac composition under a gaseous atmosphere that has reduced oxygen content, for example, no more than about 10% v/v of oxygen, allows the composition to be stored at room temperatures for a sufficiently long period of time, such as two years, without significant degradation.

Figure 2:
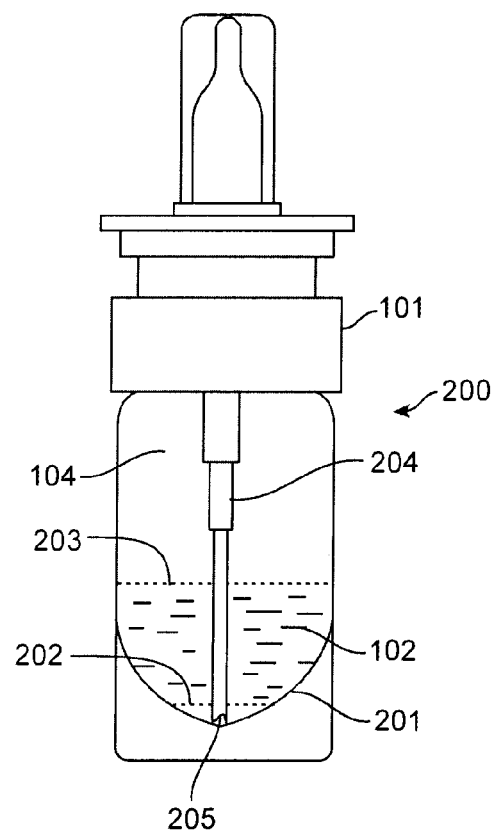
FIG. 2 illustrates an example of a high recovery vial, preferably with a head space comprising equal to or less than about 10% v/v oxygen.

A regularly shaped vial, such as the one shown in FIG. 1, has a substantially flat inner bottom. Further, there is typically a space between the tip of the dip tube and the bottom of the vial to allow liquid to flow into the dip tube. This presents multiple issues such as the need to use excess solution to ensure that adequate amounts can be delivered in each dosing for a multiple dose container as well as potential introduction of air into the dip tube thereby providing less than the desired dose. In another embodiment of this invention, there is provided a high recovery vial for nasal spray which reduces the likelihood of air being introduced into the dip tube during administration while also reducing the amount of solution required to provide adequate dosing. High recovery vials are especially beneficial where the drug composition is expensive. FIG. 2 illustrates an example of a high recovery vial 200. As shown in FIG. 2, the inner bottom of the high recovery vial 200 comprises a concave or "V" shaped bottom 201 so that residue drug solution (represented by the dashed line 202, while the dashed line 203 represents the amount of drug solution prior to use) is collected in the tip of the concave or "V" shaped bottom 201. The vial also comprises a dip tube 204 having a notch 205 to allow the solution to go into the dip tube 204. In one embodiment, the dip tube is a stiff-notched dip tube. The vial comprises a head space 104, which preferably has less than 10% v/v oxygen.

In another aspect, there is provided a nasal spray device, comprising: a vial having a volume of no more than 10 mL and a nasal spray system capped to the vial wherein the vial comprises a solution, a dip tube attached to the nasal spray system and dipping into the solution, and a head space above the solution, wherein the head space comprises no more than about 10% v/v oxygen. In some embodiments, the nasal spray device comprises the vial as described above. In preferred embodiments, the amount of oxygen in the head space is as provided above. A nasal spray device is one designed for the exit tip to be inserted into a patient's nostril to spray a defined amount of the solution into the nostril.

In some embodiments, the nasal spray device is further equipped with a metering chamber to measure a desired amount of the composition to be sprayed into the patient's nasal passage. In one embodiment, the metering chamber is coupled with the spraying device so that a patient can simultaneously measure and spray a desired amount (e.g. a unit dose) of the composition. In one embodiment, the metering chamber is able to deliver a predetermined amount of about 50 to about 125 microliters of liquid. In one embodiment, the metering chamber is able to deliver from about 50 to about 100 microliters of liquid. In one embodiment, the metering chamber having different volume deliveries can be used. In one embodiment, the metering chamber is able to measure about 50 microliters of liquid. In one embodiment, the metering chamber is able to measure about 100 microliters of liquid. Appropriate vials and spray devices with or without a metering chamber are available to one of skill in the art by referring to "Remington's Pharmaceutical Sciences." One source for such vessels is Ing. Erich Pfeiffer GmbH, Radolfzell, Germany. Another source is Valois, 50 avenue de l'Europe, 78164 MARLY-LE-ROI, France.

In another aspect, the vial or nasal spray device of this invention is in combination with labeling instructions for use in treating a pain or inflammation in a human subject. In some embodiments, the pain is the result of a trauma inflicted on the subject. In some embodiments, the pain is the result of a medical operation performed on the subject. In some embodiments, the pain is pathological. In some embodiments, the pain is neuropathic. In some embodiments, the pain is migraine or other headache pain.

Methods and Processes

In yet another aspect, there is provided a method of preparing a nasal spray device, the nasal spray device comprising: a vial having a volume of no more than 10 mL and a nasal spray system capped to the vial wherein the vial comprises a solution, a dip tube attached to the nasal spray system and dipping into the solution, and a head space above the solution, the process comprising:

a) adding a pharmaceutical composition susceptible to degradation by oxygen;

b) flowing an inert gas into the vial to purge the air out of the vial; and c) capping the vial with a nasal spray system, wherein the process results in an oxygen content in the head space of the vial equal to or less than about 10% v/v oxygen after the capping of the vial with the nasal spray system.

In some embodiments, the inert gas is nitrogen. In some embodiments, the inert gas is a noble gas, such as argon.

The following describes an efficient process to purge air from the vials, especially in a contemplated manufacturing context.

Figure 3:
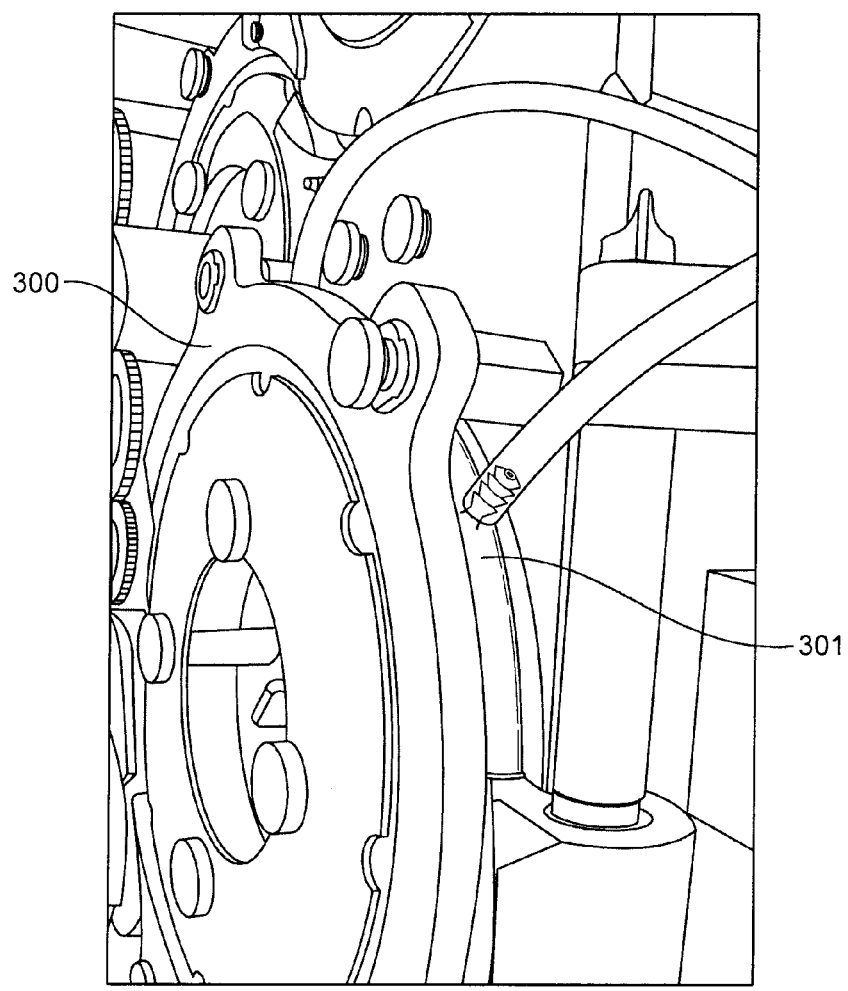
FIG. 3 illustrates an example of a conventional oxygen reduction device.

In a conventional manufacturing facility, an oxygen reduction device 300, as shown in FIG. 3, is used for purging air out of a vial containing a solution before capping of the vial, for example 100 or 200, with, for example, a cap or a spray system. In order to purge air out of the vial, a stream of an inert gas, such as argon or nitrogen, may be passed over the vial using a tube 301, also referred to as purge bar, attached to the oxygen reduction device 300. The tube 301 as attached to the oxygen reduction device 300 can be seen partially in FIG. 3.

Figure 4:
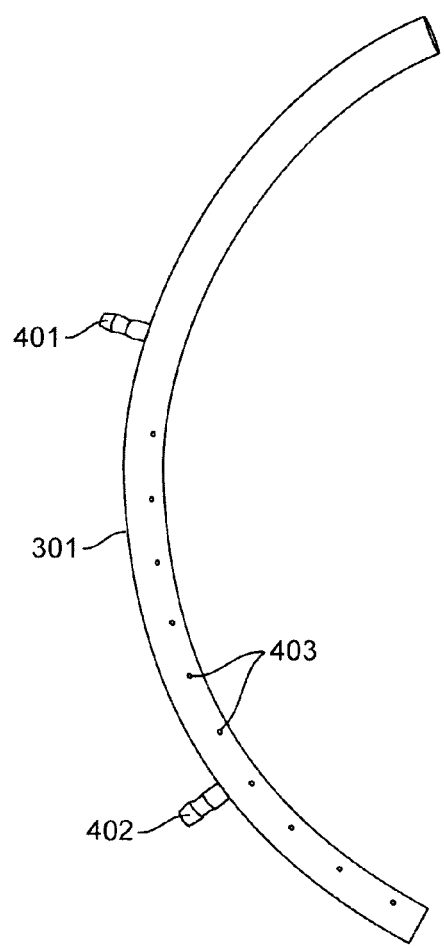
FIG. 4 illustrates a tube used in the conventional oxygen reduction device.

This tube 301 is illustrated fully in FIG. 4. The tube 301 comprises an inlet 401 and an outlet 402 and a number of holes 403 at various points in the tube 301. The nitrogen enters from the inlet 401 and passes through the tube 301 to exit through outlet 402. It is to be understood that the inlet 401 and outlet 402 can be interchanged depending on the configuration of the attached tube 301 with the oxygen reduction device 300. The holes 403 pass a stream of inert gas, such as nitrogen or argon, over the vials. Typically, in a manufacturing process, nitrogen is preferred due to cost consideration. However, the holes 403 pass the inert gas around the vials and not into the vials. Additionally, the tube 301 is attached to the oxygen reduction device 300 in such a way that the inert gas may not pass directly into the mouth of the vials but may instead be around them. In the case of nitrogen, this diffusion of the nitrogen around the vials is further coupled with the fact that the nitrogen being lighter than the air will not replace the air in the vials. This can lead to the incomplete purging of the air from the vials. This incomplete purging may be more pronounced in an aseptic environment due to rapid air flow in that situation. After the last station, where a lid or a spray system is snapped on the vial to cap the vial, a significant amount of air may remain in the vial which may lead to the degradation of the solution, such as a medicament, in the vial.

In one aspect, there is provided an improved oxygen reduction device for purging air from a vial where the vial comprises a solution and a head space, the improved oxygen reduction device comprises a tube with one or more purging outlets that flow an inert gas such as nitrogen directly over and into the vial to purge the air out of the vial, although other inert gases such as argon can be used. The following description uses nitrogen to illustrate the device and process for brevity.

Figure 5:
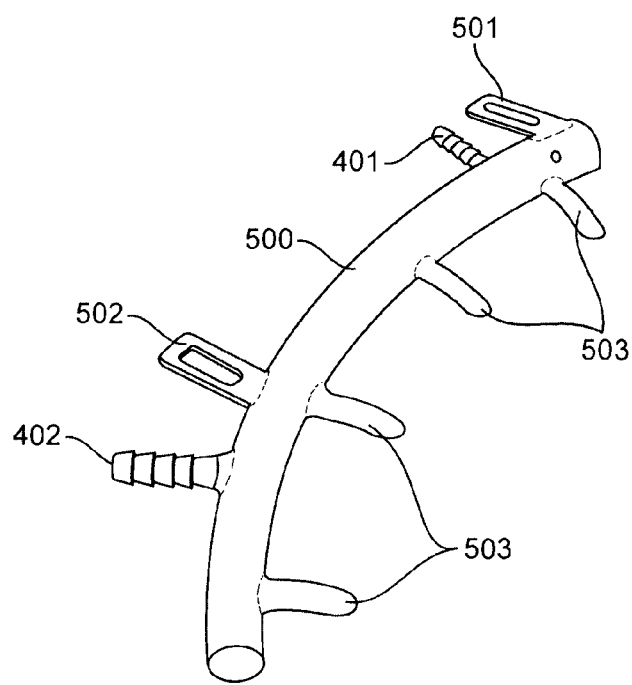
FIG. 5 illustrates a tube used in the improved oxygen reduction device.
Figure 6:
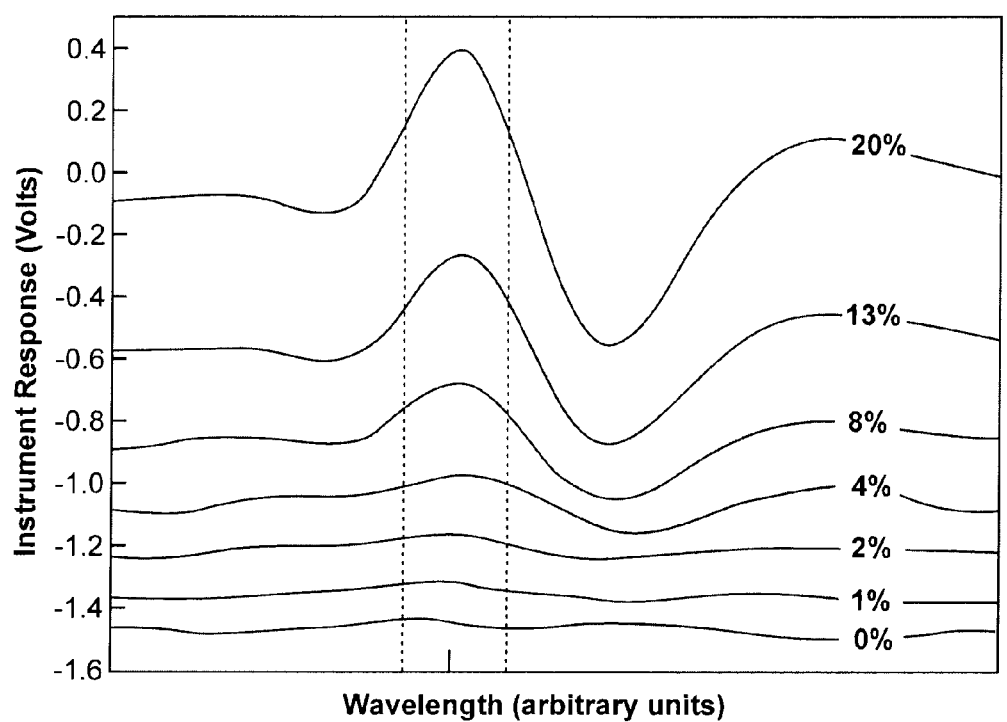
FIG. 6 illustrates an example of frequency modulation signals from oxygen absorption. The peak to peak amplitude of each spectrum is proportional to oxygen concentration (noted to the right of each scan). These spectra were taken through 1" diameter glass containers filled with certified gas mixtures of oxygen in nitrogen.

The tube 500 in the improved oxygen reduction device 300 is as illustrated in FIG. 5. The tube 500 comprises an inlet 401 and an outlet 402. The nitrogen enters from the inlet 401 and passes through the tube 500 to exit through outlet 402. It is to be understood that the inlet 401 and outlet 402 can be interchanged depending on the configuration of the attached tube 500 with the oxygen reduction device. The tube 500 optimally may comprise two brackets 501 and 502 for attaching the tube 500 to other components of the oxygen reduction device 300. The tube 500 comprises one or more purging outlets 503 (also called bar nozzles) that direct the nitrogen directly on the mouth of the vial thereby effectively purging the air out of the vial. FIG. 5 comprises four such purging outlets 503 which is for illustration purposes only. It is well understood that the number of the purging outlets 503 can vary depending on, for example, the oxygen reduction device 300 and the length of the assembly line carrying the vials along the device, etc. It is also to be understood that the design of the tube 500, inlet 401 and outlet 402, brackets 501 and 502 and purging outlets 503 in FIG. 5 is for illustration purposes only. It is contemplated that the purging outlet 503 can have different configurations so long as it can deliver nitrogen directly onto the mouth of the vial. It is also contemplated that the length and size of the purging outlet 503 and/or the position of the vial may be adjusted so that the distance between the tip of the purging outlet 503 and the mouth of the vial can be optimal for delivering nitrogen inside the vial.

In some embodiments, the tube 500 has at least two purging outlets 503. In some embodiments, the tube 500 has at least three purging outlets 503. In some embodiments, the tube 500 has four purging outlets 503. The tube 500 can be made of materials well known in the art. For example, the tube 500 can be made of stainless steel. In some embodiments, the tube 500 is made of plated metal. It is important that the purging outlets 503 are oriented in such a manner that the distal end of the purging outlet 503 is placed over the mouth of the vial. In some embodiments, at least one purging outlet 503 of the tube 500 is close to a last station where a capping of the vial with the spray system takes place in order to minimize oxygen reentry into the gaseous atmosphere in the vial. The orientation of the purging outlet 503 should be combined with a capping system such that capping occurs within 1 second of purging and preferably within 0.6 seconds of purging and even more preferably from 0.3 seconds to 0.5 seconds, and most preferably 0.4 second.

The one or more purging outlets 503 of the tube 500 in the oxygen reduction device 300, as illustrated in FIG. 5, flow nitrogen directly over and into the vial to purge the air out of the vial thereby reducing an oxygen content in the head space of the vial to equal to or less than about 10% v/v oxygen. In some embodiments, the reduction in the oxygen content in the head space of the vial to equal to or less than about 10% v/v oxygen is an improvement over a conventional oxygen reduction device wherein the reduction in the oxygen content in the head space of the vial is more than about 10% v/v oxygen. In some embodiments, the reduction in the oxygen content in the head space of the vial is equal to or less than about 8% v/v oxygen; equal to or less than about 5% v/v oxygen. In some embodiments, the reduction in the oxygen content in the head space of the vial is in the range of about 5-10%, 3-8% or 2-5% v/v.

In some embodiments, the improvement in the oxygen reduction device further comprises adjusting a flow rate of the nitrogen to reduce the oxygen content in the vial. The flow rate of the nitrogen can be increased or decreased depending on the purging of the air out of the vial. This adjustment of the nitrogen flow can help reduce the oxygen content in the vial. In some embodiments, the nitrogen flow rate is about 20 liters per minute (L/min) to about 80 L/min. In some embodiments, the nitrogen flow rate is about 40 L/min to 60 L/min. In some embodiments, the nitrogen flow rate is about 50 L/min.

In some embodiments, the improvement in the oxygen reduction device further comprises adjusting a speed of a capping of the vial, such as with a nasal spray system. In some embodiments, the capping rate is selected to permit purging of from about 100 vials per minute to about 210 vials per minute. In some embodiments, the capping rate is about 150 vials per minute to about 210 vials per minute. In some embodiments, the capping rate is selected to permit purging of about 150 vials per minute. The adjustment of the speed of the capping may also comprise attaching a purging outlet 503 in FIG. 5 closer to the last station where the capping of the vial takes place. By attaching the purging outlet 503 closer to the last station, the time lag between the vial leaving the assembly line and reaching the capping end can be reduced thereby reducing the amount of time the vial is exposed to air. In some embodiments, the nitrogen is blown into the vial simultaneously with capping the vial. This improvement can further reduce the oxygen content in the vial.

Provided herein is also a process to purge air from a vial, especially in an aseptic environment, the vial comprising a solution and a head space, the process comprising: flowing an inert gas, such as nitrogen or argon, directly over and into the vial to purge the air out of the vial using an improved oxygen reduction device wherein the device comprises a tube with one or more purging outlets that flow the inert gas directly over and into the vial to purge the air out of the vial, wherein the process reduces an oxygen content in the head space of the vial to equal to no more than about 10% v/v oxygen.

Provided herein is also a process to manufacture a nasal spray device, especially in an aseptic environment, the nasal spray device comprising: a vial and a nasal spray system capped to the vial wherein the vial comprises a solution, a dip tube attached to the nasal spray system and dipping into the solution, and a head space above the solution, the process comprising:

a) providing the vial to an improved oxygen reduction device wherein the improved oxygen reduction device comprises a tube with one or more purging outlets that flow nitrogen directly over and into the vial to purge the air out of the vial;

b) flowing an inert gas, directly over and into the vial to purge the air out of the vial; and c) capping the vial with a nasal spray system;

wherein the process reduces an oxygen content in the head space of the vial to equal to or less than about 10% v/v oxygen after the capping of the vial with the nasal spray system.

In some embodiments, the inert gas is nitrogen. In some embodiments, the inert gas is a noble gas. In some embodiments, the inert gas is argon. In some embodiments, the rate of capping is selected to be fast enough to ensure that minimal atmospheric change occurs in the vial between completion of the purging and capping and slow enough to ensure that the purging process is effective. In some embodiments, capping occurs within about 0.28 to 1 second after purging so as to provide for 60 to 210 vials capped per minute; preferably within about 0.28 to 0.4 seconds (150 to 210 vials capped per minute).

In some embodiments, all or a selected number of the treated and capped vials are passed through spectrometry analysis to measure the oxygen content and/or further remove the vials with unacceptable oxygen content.

Compositions Useful in the Invention

In some embodiments, the solution inside the vial is an intranasal formulation of ketorolac or a pharmaceutically acceptable salt thereof. In some embodiments, the bacterial load in the solution is less than about 100 colony forming units (CFU).

In some embodiments, the intranasal formulation comprises concentrations of ketorolac, or a pharmaceutically acceptable salt, ranging from about 12.5 to 38% weight to volume (w/v), for example about 15%, 20%, 25%, 28%, 29%, 30%, 31%, 32%, 33%, 34%, 35%, 36%, 37%, or 38% w/v, based on the final formulation.

In some embodiments, the intranasal formulation comprises:
(a) about 12.5% w/v to about 38% w/v of ketorolac or a pharmaceutically acceptable salt thereof, and
(b) a pharmaceutically acceptable carrier.

In some embodiments, the composition further comprises a local anesthetics, such as lidocaine, or a pharmaceutically acceptable salt, ranging from about 4% to 10%, for example about 4%, 5%, 6%, 7%, 8%, 9%, or 10% w/v. As disclosed in US Patent Application Publication No. 2009/0042968, which is incorporated herein by reference in its entirety, the addition of lidocaine to the 15% ketorolac composition has been found to provide unexpected advantageous synergistic effects. First, the combination substantially reduces the stinging sensation caused by ketorolac. Second, while lidocaine is a local anesthetic that is known to cause numbness, such numbness is substantially absent or reduced when lidocaine is combined with ketorolac. Third, combination of 5 to 6% of lidocaine with ketorolac have been found to decrease the Tmax for ketorolac to reach its Cmax in a subject's plasma, providing a subject with faster and better pain relief. It is contemplated that when the concentration of ketorolac is increased to up to about 38%, the amount of lidocaine can be maintained at a level of 4-10% or preferably 5-6% and yet still inhibits the stinging sensation of ketorolac.

In some embodiments, the intranasal formulation comprises:
(a) about 12.5% w/v to about 38% w/v of ketorolac or a pharmaceutically acceptable salt thereof,
(b) about 4% w/v to about 10% w/v of lidocaine or a pharmaceutically acceptable salt thereof, and
(c) a pharmaceutically acceptable carrier.

In some embodiments, ketorolac is as a racemic mixture. In some embodiments, the pharmaceutically acceptable salt of ketorolac is ketorolac tromethamine. In some embodiments, the intranasal formulation comprises about 13% to 20% w/v of ketorolac tromethamine. In some embodiments, the intranasal formulation comprises about 15% w/v of ketorolac tromethamine. In some embodiments, the intranasal formulation comprises about 25% to 35% w/v of ketorolac tromethamine. In some embodiments, the intranasal formulation comprises about 28% to 32% w/v of ketorolac tromethamine. In some embodiments, the intranasal formulation comprises about 30% w/v of ketorolac tromethamine.

In some embodiments, the intranasal formulation comprises lidocaine hydrochloride. In some embodiments, the intranasal formulation comprises about 5-6% lidocaine hydrochloride. In some embodiments, the intranasal formulation comprises about 6% lidocaine hydrochloride.

In some embodiments, the intranasal formulation further comprises a chelator, i.e. a substance that binds primarily di- or tri valent metallic ions (e.g. calcium) that might interfere with the stability or activity of the active ingredient. Chelators are known to those of skill in the art by referring to the recent edition of "Remington's Pharmaceutical Sciences." A preferred chelator is sodium ethylenediamine tetraacetic acid (sodium EDTA), USP. In some embodiments, the chelator is disodium edetate.

In some embodiments, the pH of the intranasal formulation is about 4.5 to 8. In some embodiments, the pH is about 4.8 to 7.5. In some embodiments, the pH is about 7.2.

In some embodiments, the pH is adjusted by a pharmaceutically acceptable base. In some embodiments, the pharmaceutically acceptable base is sodium hydroxide.

A pharmaceutically acceptable buffer may be present in order to create optimum pH conditions for both product stability and tolerance (pH range about 4 to about 8; preferably about 6.0 to 7.5). Suitable buffers include without limitation tris (tromethamine) buffer, phosphate buffer, etc. Preferably potassium phosphate NF is used to adjust the pH to 7.2. In some embodiments, the composition comprises up to about 2% of a phosphate buffer, such as potassium phosphate monobasic, potassium phosphate dibasic. In some embodiments, the composition comprises about 0.6 to 0.8% w/v of potassium phosphate monobasic. In some embodiments, the composition comprises about 0.68% w/v of potassium phosphate monobasic.

In some embodiments, the intranasal formulation is a sprayable liquid.

In some embodiments, the pharmaceutically acceptable carrier is water.

In some embodiments, the intranasal formulation comprises:
(a) about 15% w/v of racemic ketorolac tromethamine,
(b) about 0.01% w/v to about 0.1% w/v of disodium edetate,
(c) about 0.68% w/v of potassium phosphate monobasic,
(d) sodium hydroxide to adjust the pH to 7.2, and
(e) water to 100% w/v.

In some embodiments, the intranasal formulation comprises:
(a) about 15% w/v of racemic ketorolac tromethamine,
(b) about 5% w/v to about 6% w/v lidocaine hydrochloride,
(c) about 0.01% w/v to about 0.1% w/v of disodium edetate,
(d) about 0.68% w/v of potassium phosphate monobasic,
(e) sodium hydroxide to adjust the pH to 7.2, and
(f) water to 100% w/v.

In some embodiments, the intranasal formulation comprises:
(a) about 30% w/v of racemic ketorolac tromethamine,
(b) about 0.01% w/v to about 0.1% w/v of disodium edetate,
(c) about 0.68% w/v of potassium phosphate monobasic,
(d) sodium hydroxide to adjust the pH to 7.2, and
(e) water to 100% w/v.

In some embodiments, the intranasal formulation comprises:
(a) about 30% w/v of racemic ketorolac tromethamine,
(b) about 5% w/v to about 6% w/v lidocaine hydrochloride,
(c) about 0.01% w/v to about 0.1% w/v of disodium edetate,
(d) about 0.68% w/v of potassium phosphate monobasic,
(e) sodium hydroxide to adjust the pH to 7.2, and
(f) water to 100% w/v.

The intranasal formulation may optionally comprise one or more pharmaceutically acceptable excipients. The preferred diluent for the formulations is water, and other excipients may be added if desired.

In addition to aqueous, oil or gel diluents, other diluents which may be used in the intranasal formulation comprise solvent systems containing ethyl alcohol, isopropyl alcohol, propylene glycol, polyethylene glycol, mixtures thereof or mixtures of one or more of the foregoing with water.

Other excipients include chemical enhancers such as absorption promoters. These include fatty acids, bile acid salts and other surfactants, fusidic acid, lysophosphatides, cyclic peptide antibiotics, preservatives, carboxylic acids (ascorbic acid, amino acids), glycyrrhetinic acid, o-acylcarnitine. Preferred promoters are diisopropyladipate, POE(9) lauryl alcohol, sodium glycocholate and lysophosphatidyl choline which proved to be particularly active.

If present, excipients such as oil, gel, chemical enhancers, including absorption promoters, etc. should be in an amount that does not adversely affect the homogeneity and sprayability of the solution.

The intranasal formulation can also contain a compatible preservative that ensures the microbiological stability of the active ingredient. Suitable preservatives include without limitation, methyl paraoxybenzoate (methyl paraben), propyl paraoxybenzoate (propyl paraben), sodium benzoate, benzyl alcohol, and chlorobutanol. In one embodiment, the intranasal ketorolac formulation does not contain a preservative.

Illustrative formulations may contain the following ingredients and amounts (w/v) in addition to ketorolac, lidocaine and water.

| Ingredient | Broad Range (%) | Preferred Range (%) |
|---|---|---|
| Chelator (1) | 0.001-1 | 0.01-0.1 |
| Preservative (2) | 0-2 | 0-0.25 |
| Absorption promoter (3) | 0-10 | 0-10 |
| Gelling polymer (4) | 0-5 | 0-3 |
| Co-solvent (5) | 0-99 | 0 |

(1) E.g., sodium EDTA
(2) E.g., methyl paraoxybenzoate or propyl paraoxybenzoate or mixtures thereof
(3) E.g., sodium glycocholate
(4) E.g., sodium CMC
(5) E.g., glycerol The following examples are provided to illustrate certain aspects of the present invention and to aid those of skill in the art in practicing the invention. The examples are in no way to be considered to limit the scope of the invention.

EXAMPLE

Example 1

Headspace Oxygen Analysis

Headspace oxygen concentrations were measured using a Lighthouse Instruments FMS-760 Headspace Oxygen Analyzer. The measurements were made to assess the performance of a nondestructive measurement method for headspace oxygen analysis.

Instrumentation and Method

Laser Absorption Spectroscopy:

Laser absorption spectroscopy is an optical measurement method for rapid and non-invasive headspace gas analysis of containers, such as parenteral containers or containers for intranasal spray. The technique can measure a number of physical parameters within the headspace of the container, including gas concentrations and total headspace pressures.

Light from a near-infrared semiconductor laser is tuned to match the internal vibrational frequency of the target molecule. The light is passed through the headspace region of a container, scanned in frequency and detected by a photodetector. The amount of light absorbed is proportional to the target molecule concentration.

The instruments incorporate a high sensitivity detection method known as frequency modulation spectroscopy.

Oxygen Absorption Spectroscopy: General

Oxygen absorbs near infrared light in a band of transitions centered at 0.762 µm. The oxygen A-band is a series of rotational transitions within the 0-0 vibrational band of the $X^3\Sigma^-_g \leftarrow b^1\Sigma^+_g$ magnetic dipole transition.

Headspace Oxygen Measurements

Measurement Principle

The amount of laser light absorbed by an individual transition in the oxygen A-band is proportional to the oxygen concentration in the headspace of a parenteral or nasal spray container. In general the laser frequency is repeatedly scanned over the absorption feature and successive scans are averaged to improve the signal to noise ratio. The averaged light absorption signal (an example shown in FIG. 6) and the total power are then multiplied by a calibration constant to yield the headspace oxygen concentration.

Instrument Calibration

An instrument calibration constant, k, is determined using a vial filled with a known concentration of oxygen. Oxygen standards are prepared using certified gas mixtures of oxygen and nitrogen. A 20% oxygen/80% nitrogen standard is used for FMS-760 calibration.

A calibration standard is inserted to the instrument, the system response (signal amplitude, S, and power, P) is measured and a calibration constant is computed.

The instrument calibration procedure is fully automated and controlled by the instrument computer. Once the user inputs the calibration vial and initiates the calibration routine the instrument begins to record data and using the known concentration computes a calibration constant k, $$k=(P/S)\cdot\text{Known Concentration} \quad [1]$$

where P is the detected laser power, S is the peak to peak absorption signal (see FIG. 6 for oxygen example), and Known Concentration is the concentration in the calibration vial. The measured values of P and S are the average of 1000 scans (10 s acquisition time). The system stores the calibration constant and uses it for subsequent sample measurements.

Measurements

The instrument data acquisition system uses the stored calibration constant to determine the headspace oxygen concentration in a sample. When a sample with an unknown concentration is inserted to an instrument the system measures the absorption signal and laser power and multiplies by the calibration constant to determine the headspace oxygen or water vapor concentration.

$$\%\ \text{Oxygen in Sample} = (S_m/P_m)\cdot k \quad [2]$$

$$= (S_m/P_m)\cdot(P_c/S_c)\cdot\%\ \text{Oxygen in Standard} \quad [3]$$

where $S_m$ is the sample signal amplitude, $P_m$ is the laser power transmitted through the sample, $P_c$ is the calibration power and $S_c$ is the calibration signal amplitude, % Oxygen in Standard is the known amount of oxygen in the calibration vial.

Measurement Protocol

Headspace oxygen measurements were performed using a Lighthouse Instruments FMS-760 Headspace Oxygen Analyzer (SN 760-104). The instrument was turned on and allowed to warm up for thirty minutes. Calibration was performed using a 21% oxygen standard. The headspace oxygen concentration in each sample was measured three times.

Example 2

Reduction of Oxygen Content in the Head Space of a Vial

A suitable length of a tubing, preferably made of a chemical resistant polymer and preferably free from contamination, is connected to an argon or nitrogen gas tank at one end. The other end of the tubing is inserted in the mouth of a vial having a ketorolac solution and an about 2 mL head space, preferably the tubing does not touch the ketorolac solution inside the vial. Argon or nitrogen is passed through the tubing into the vial for a sufficient amount of time so that the oxygen content in the head space of the vial is less than 10%. The tubing is removed from the vial and the vial is capped with a nasal spray system and stored at room temperature.

Example 3

Oxygen Content in the Head Space of Vials Purged by a Conventional Oxygen Reduction Device in an Assembly Line Vials were processed using a conventional oxygen reduction device having a tube with purging holes. Other conditions are the same as described in Example 4 below. The oxygen content of the following five sets of glass vials were tested using the above described protocol of Example 1. The individual results were recorded and averaged and mean concentration and standard deviation were computed. The results of the samples tested are summarized below.

Set 1: Five 4 mL Clear Glass Vials Containing a 2 mL Fill of Solution with Nitrogen Overlay The individual headspace oxygen measurements of the five samples varied from between 17.8% to 20.5%, and the average headspace oxygen concentrations of the each of the five samples varied between 18.3% and 20.2%, with a mean of 19.0% and a standard deviation of 0.80%.

Set 2: Five 4 mL Clear Glass Vials Containing a 2 mL Fill of Solution without Nitrogen Overlay The individual headspace oxygen measurements of the five samples varied from between 20.2% to 21.7%, and the average headspace oxygen concentrations of each of the five samples varied between 20.6% and 21.1%, with a mean of 20.8% and a standard deviation of 0.20%.

Set 3: Five 4 mL Clear Glass Vials Containing a 2 mL Fill of Solution with Nitrogen Overlay Set 3 is a repeat of Set 1, except that in Set 3 the samples were collected after stopping the capper (simulated line stoppage) for 5 minutes and resuming the capping operation.

The individual headspace oxygen measurements of the five samples varied from between 18.2% to 22.0%, and the average headspace oxygen concentrations of each of the five samples varied between 18.7% and 21.4%, with a mean of 19.5% and a standard deviation of 1.11%.

Set 4: Five Empty 4 mL Clear Glass Vials with Nitrogen Overlay

The individual headspace oxygen measurements of the five samples varied from between 20.5% to 21.9%, and the average headspace oxygen concentrations of each of the five samples varied between 18.4% and 21.8%, with a mean of 19.9% and a standard deviation of 1.46%.

Set 5: Five Empty 4 mL Clear Glass Vials without Nitrogen Overlay

The individual headspace oxygen measurements of the five samples varied from between 18.1% to 21.7%, and the average headspace oxygen concentrations of each of the five samples varied between 21.1% and 21.4%, with a mean of 21.3% and a standard deviation of 0.12%.

Example 4

Oxygen Content in the Head Space of Vials Purged by an Improved Oxygen Reduction Device This experiment was conducted to determine optimal nitrogen flow at capping rates of 150 and 210 vials per minute utilizing an improved oxygen reduction device of this invention. Further engineering changes within the skill in the art can be applied to generate commercial or manufacture devices.

The experiment was conducted using 20 mm Hi-Recovery vials (4 mL) and snap-on metering pump. The vials were filled with about 1.8 mL of injection quality water (WFI) while purged with nitrogen having varying flow rates. The experiment was repeated with a similar oxygen reduction device having GMP quality. Twenty vials from each fill speed and flow rate combination were sampled and tested. Result summaries are shown in the following tables 1 and 2.

TABLE 1

150 Vials per Minute - Results in % $O_2$ (v/v)

|  | 0 L/min | 20 L/min | 40 L/min | 60 L/min | 80 L/min |
| --- | --- | --- | --- | --- | --- |
| Average* | 20.49 | 9.53 | 6.89 | 6.69 | 6.78 |
| Minimum** | 19.83 | 8.49 | 6.10 | 5.25 | 5.42 |
| Maximum*** | 21.17 | 12.45 | 9.52 | 9.22 | 10.27 |

TABLE 2

210 Vials per Minute - Results in % $O_2$ (v/v)

|  | 0 L/min | 20 L/min | 40 L/min | 60 L/min | 80 L/min |
| --- | --- | --- | --- | --- | --- |
| Average* | 20.60 | 11.03 | 9.23 | 7.49 | 8.14 |
| Minimum** | 19.99 | 8.01 | 6.99 | 6.29 | 6.66 |
| Maximum*** | 21.57 | 13.66 | 19.29 | 13.42 | 17.03 |

*"Average" indicates the average $O_2$ content in the tested vials for the respective group.
**"Minimum" indicates the $O_2$ content of the vial with the lowest $O_2$ content in the respective group.
***"Maximum" indicates the $O_2$ content of the vial with the highest $O_2$ content in the respective group.

The data show all vials prepared using the 150 vials per minute rate had an oxygen content of less than 13% and all vials prepared with flow rates at 40 and 60 L/min had an oxygen content of below the 10%.

The data show that the capping rate is one of the critical parameters in ensuring that the head space of the vials maintains an oxygen concentration of 10% v/v or less. The results indicate that oxygen contents for the vials run at 150 vials per minute were generally lower than the same settings at 210 vials per minute. It is contemplated that capping speeds would directly affect the amount of retention time each vial has under the oxygen reduction device bar nozzles. In addition, at the high machine speed (210 vials per minute), frequent pauses were observed as the pump bowl was not supplying pumps at the same rate. This may have caused the high oxygen contents in some of the vials prepared at a rate of 210 vials per minute. It is anticipated that adjusted operation of the pump bowl would reduce the frequency and duration of the pauses, which would result in tighter oxygen level results. Another solution is to reject vials after machine stoppage.

Residual oxygen contents for 80 L/min at both speeds were slightly higher than those observed at the 60 L/min flow. As flow rate gets higher, the volume that can be displaced is higher, but the flow also grows more turbulent, possibly entraining ambient air with the purge air.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for reducing ketorolac degradation under ambient conditions wherein said ketorolac is in an aqueous composition maintained in an enclosed vial having a defined gaseous headspace and containing from about 12 to 38% w/v ketorolac wherein the method comprises:
   a) placing said ketorolac vial on an assembly line;
   b) moving the vial on said assembly line wherein the vial is exposed to a flow of an inert gas directly over and into the vial to purge at least a portion of the oxygen out of the vial and subsequently capping the vial, wherein the rate of the gas flow and capping process are adjusted such that the amount of oxygen remaining in the head space of the capped vial is about 5-10% v/v; and
   c) capping the vial.

2. The method of claim 1, wherein the inert gas is nitrogen.

3. The method of claim 1, wherein the inert gas is a noble gas.

4. The method of claim 3, wherein the inert gas is argon.

5. The method of claim 1, wherein the ketorolac aqueous composition is preserved for at least 2 years at room temperature.

6. The method of claim 1, wherein from about 100 to about 210 purged vials are capped per minute.

* * * * *